US00PP34672P2

(12) United States Plant Patent
Chandra et al.

(10) Patent No.: US PP34,672 P2
(45) Date of Patent: Oct. 18, 2022

(54) HYBRID BLUEGRASS NAMED 'DALBG 1201'

(50) Latin Name: ***Poa arachnifera* Torr.x *P. pratensis* L.$F_1$ hybrid**
Varietal Denomination: DALBG 1201

(71) Applicant: The Texas A&M University System, College Station, TX (US)

(72) Inventors: Ambika Chandra, McKinney, TX (US); James C. Read, Medina, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 17/242,507

(22) Filed: Apr. 28, 2021

(51) Int. Cl.
*A01H 6/46* (2018.01)
*A01H 5/12* (2018.01)

(52) U.S. Cl.
USPC ..... Plt./393

(58) Field of Classification Search
USPC ..... Plt./393
See application file for complete search history.

(56) References Cited

U.S. PATENT DOCUMENTS

PP18,439 P2 1/2008 Hardison et al.
PP18,467 P2 1/2008 Hardison et al.

OTHER PUBLICATIONS

Registration of DALBG 1201 Hybrid Bluegrass Journal of Plant Registrations . Jan. 16, 2015.*

Meeks et al. Growth Responses of Hybrid Bluegrass and Tall Fescues as influenced by light intensity and Trnexapac-Ethyl American Society For Horticultural Science Hortscience Journal 2015.*

U.S. Appl. No. 17/242,515, filed Apr. 28, 2021, Chandra et al.

Meeks et al., "The application of flow cytometry and a thioredoxin-like nuclear gene for breeding *Poa arachnifera* × *Poa pratensis* hybrids." Plant Breeding, 2015, 134(5), pp. 612-622.

Meeks et al., "Growth Responses of Hybrid Bluegrass and Tall Fescue as Influenced by Light Intensity and Trinexapac-ethyl." HortScience, 2015, 50(8), pp. 1241-1247.

Kentucky Bluegrass 'Reveille', PVP Certificate No. 9800337, issued Jul. 23, 2004.

M. Meeks et al., "Registration of DALBG 1201 Hybrid Bluegrass," Journal of Plant Registrations, 2015, 9(2), 138-143.

* cited by examiner

*Primary Examiner* — Annette H Para
(74) *Attorney, Agent, or Firm* — Dentons US LLP

(57) ABSTRACT

'DALBG 1201' is an $F_1$ hybrid bluegrass with exceptional turfgrass quality, dark green color, high shoot density, medium-fine leaf texture, and ability to persist under a range of environmental stresses typically encountered in the southern United States.

10 Drawing Sheets

Latin name of the genus and species of the plant claimed: *Poa arachnifera* Torr.x *P. pratensis* L.$F_1$ hybrid.

Variety denomination: 'DALBG 1201'.

BACKGROUND OF THE INVENTION

The *Poa* genus includes approximately 200 to 300 species, both annual and perennial types, that are native to temperate regions of northern and southern hemispheres. Of these, Kentucky bluegrass (*Poa pratensis* L.) is the predominant perennial species of *Poa* used in the United States for turf and forage applications. Although it displays excellent turfgrass quality, its use in southern climates is limited because of its sensitivity to heat and drought stress. Texas bluegrass is well known for its heat and drought tolerance and is native to the southern region of the United States spanning from New Mexico to South Carolina. The first successful attempt to genetically improve stress tolerance in Kentucky bluegrass was made in 1908 by George Oliver (Vinall and Hein, 1937) by hybridizing Kentucky bluegrass with Texas bluegrass (*P. arachnifera* Torr.); however, it was not until 1998, 90 years later, that the first commercially available interspecific hybrid between Texas bluegrass and Kentucky bluegrass, 'Reveille', was developed (Read et al., 1999; PVP Certificate No. 9800337). This large span of time can be attributed to the limited amount of knowledge available for the two species as it pertains to their morphological and agronomic characteristics, as well as the complexity of their genetic compositions.

Members of the genus *Poa* exhibit different ploidy levels, diploid, polyploid, or aneuploid, with a basic chromosome number of x=7. There is great variation in chromosome number both within and among species of *Poa* (Patterson et al., 2005). Kentucky bluegrass is documented to have chromosome numbers ranging from 2n=24 to 124 (Love and Love, 1975), and Texas bluegrass chromosome numbers range from 2x=42 to 91 (Hartung, 1946; Kindiger et al., 2011).

Even though greater success in hybridization may be achieved when high polyploid parents such as Kentucky bluegrass are used as pollinators (Pepin and Funk, 1974), extreme differences in ploidy levels is still one of the greatest barriers to successful interspecific hybridization in *Poa* (Kelley et al., 2009).

Kentucky bluegrass primarily produces seed asexually through apomixis, although it does produce sexual seed at a low frequency (Grazi et al., 1961; Han, 1969, Wieners et al., 2006), and is referred to as a facultative apomict. 'Reveille' has been shown to produce 90% of its seed apomictically (Read et al., 1999). In contrast to Kentucky bluegrass, Texas bluegrass is a sexually obligate dioecious species with separate female and male plants present in the breeding population. Since the release of 'Reveille', other hybrid bluegrass cultivars with specific improvements in heat and drought tolerance, and disease resistance, have been developed, including 'Bandera' (Smith et al., 2008) and 'Thermal Blue' (also known as 'HB129'; U.S. Plant Pat. No. 18,467).

SUMMARY OF THE INVENTION

The present disclosure relates to a new and distinct interspecific *Poa arachnifera* Torr. x *P. pratensis* L. $F_1$ hybrid variety named 'DALBG 1201'. 'DALBG 1201', formerly tested as TAES 5653 and 01-59-5, was produced in 2001 near Dallas, Tex. by fan-mediated bag crossing between Texas bluegrass ecotype 20-11 (3-88) (PI 655088) (unpatented) as the female parent and Kentucky bluegrass ecotype CS#4 (unpatented) as the male parent (pollen). 'DALBG 1201' represents a single genotype from a family of 16 progeny. 'DALBG 1201' was first asexually propagated in Dallas, Tex. by propagating vegetative material into smaller plugs and allowing the plugs to grow before splitting them again.

'DALBG 1201' is an experimental Texas bluegrass× Kentucky bluegrass interspecific hybrids developed at the Texas A&M AgriLife Research and Extension Center in Dallas, Tex., which was evaluated over a 3-year period (2010-2012) alongside 46 other experimental Texas bluegrass×Kentucky bluegrass interspecific hybrids; five Texas bluegrass ecotypes (TAES 5679, 5681-5684); six Kentucky bluegrass genotypes (H8G-J86, PTDF-22-B-2, H86-712, TAES 5701, 5706, and 5709); two commercial hybrid bluegrass checks ('Reveille', 'Thermal Blue Blaze'); and 'Rebel Exeda' tall fescue. The evaluations took place in multiple locations with test sites located in Auburn, Ala.; Dallas, Tex.; Starkville, Miss.; Raleigh, N.C.; and Knoxville, Tenn.

The turfgrass quality for DALBG 1201 was statistically superior to 'Reveille' and 'Thermal Blue Blaze' in four test locations (Auburn, Ala., Starkville, Miss., Raleigh, N.C., Dallas, Tex.), and was in the same statistical group in Knoxville, Tenn. (Table 3). The turfgrass quality of DALBG 1201 was statistically similar to 'Rebel Exeda' at Auburn, Starkville, and Knoxville and was superior in Dallas. When averaged across all locations, the turfgrass quality of DALBG 1201 was statistically superior than the commercial checks 'Thermal Blue Blaze', 'Reveille', and 'Rebel Exeda'. 'DALBG 1201' differs from its parents and all other known *Poa arachnifera* Torr. x *P. pratensis* L. $F_1$ hybrid cultivars.

The following are the most outstanding and distinguishing characteristics of 'DALBG 1201': It exhibits a combination of (1) exceptional turfgrass quality, (2) dark green color, (3) high shoot density, (4) medium-fine leaf texture, (5) drawf canopy, and (6) the ability to persist under a range of environmental stresses typically encountered in the southern United States. 'DALBG 1201' turf can also be distinguished at least based upon its above-acceptable turfgrass quality and reduced leaf-elongation rate under full-sun as well as in moderately and heavily shaded environments.

'DALBG 1201' turf can be distinguished from Texas bluegrass ecotype 20-11 (3-88) turf (female parent) at least based upon their floret characteristics. Specifically, ecotype 20-11 (3-88) only has female reproductive organs in its florets; while DALBG 1201 has a perfect flower with both male and female reproductive organs in its florets. Additionally, DALBG 1201 has finer leaf-texture, darker green cover, and dwarf canopy as compared to its female parent 20-11 (3-88). 'DALBG 1201' turf can be distinguished from Kentucky bluegrass ecotype CS#4 turf (male parent) at least based upon the thioredoxin-like nuclear gene molecular marker.

BRIEF DESCRIPTION OF THE DRAWINGS

'DALBG 1201' is illustrated by the accompanying photographs, which show the turfgrass quality analysis of 'DALBG 1201' as well as the claimed plant's vegetative and floral characteristics. The colors shown are as true as can be reasonably obtained by conventional photographic procedures.

DETAILED BOTANICAL DESCRIPTION

Figure 1:
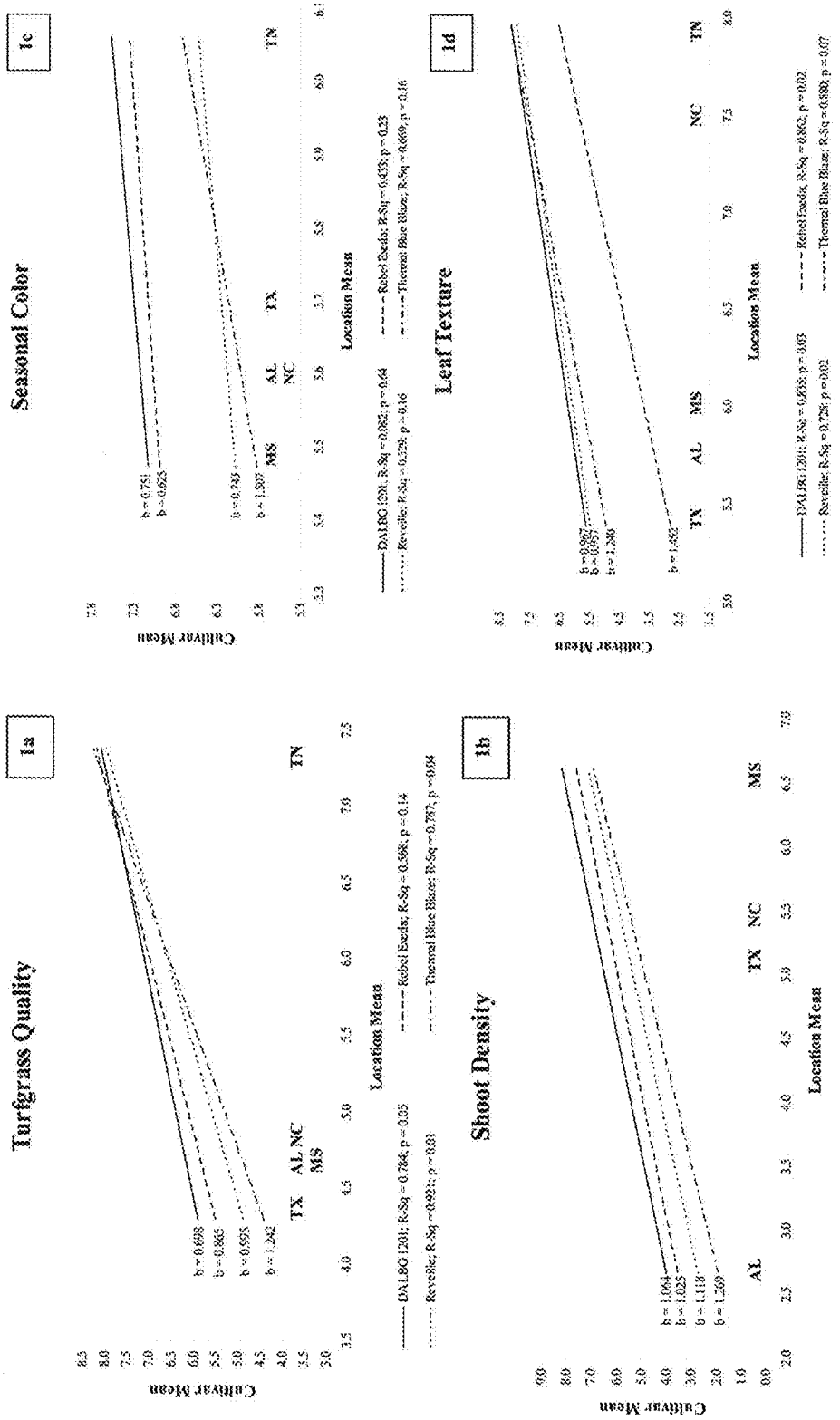
FIG. 1—Shows the Genotype×Environment Stability Analysis of DALBG 1201 and the three commercial checks 'Rebel Exeda', 'Reveille', and 'Thermal Blue Blaze' for (a) turfgrass quality, (b) shoot density, (c) seasonal color, and (d) leaf texture.

The following detailed description sets forth the distinctive characteristics of 'DALBG 1201'. The claimed plant was four months old when the data was collected in Dallas, Tex. Color references are to the Munsell Color Chart; 1977 Edition of the Munsell Color Charts for Plant Tissues, unless otherwise indicated. Color designations provided refer to both mature and immature stages unless otherwise indicated. If any Munsell color designations below differ from the accompanying photographs, the Munsell color designations are accurate.

Plant:

*Growth habit.*—Semi-erect.

*Growth habit after vernalization.*—Semi-erect.

*Natural plant height (at maturity).*—34.8 cm.

*Plant height before stem elongation.*—17.8 cm.

*Tillers on the culm.*—None.

*Self-fertility.*—Female sterile.

Rhizomes:

$1^{st}$ *internode length.*—11.74 mm.

$2^{nd}$ *internode length.*—15.76 mm.

3rd *internode length.*—13.77 mm.
4th *internode length.*—12.11 mm.
4th *internode diameter.*—0.58 mm.
4th *node diameter.*—1.04 mm.

Leaves:
*Length* (*flag leaf*).—2.4 cm.
*Width* (*flag leaf*).—2.26 mm.
*Leaf Curling.*—None.
*Leaf sheath pubescence.*—Absent.
*Leaf sheath hairs on surface.*—Absent.
*Leaf sheath hairs on margin.*—Absent.
*Leaf sheath margin roughness* (*to touch*).—Smooth.
*Leaf sheath surface roughness* (*to touch*).—Smooth.
*Leaf sheath hairs just beneath leaf blade* (*under collar*).—Absent.
*Leaf sheath color.*—Green; Munsell color 2.5G value of 5 and chroma of 5.
*Leaf collar color.*—Munsell color 5 GY color of 7 and chroma of 6.
*Anthocyanin coloration of the basal leaf sheath.*—Absent.
*Lower surface leaf coloration.*—Munsell color 2.5G value of 4 chroma of 6.
*Upper surface leaf coloration.*—Munsell color 2.5G value of 3 chroma of 4.
*Auricles.*—Absent.
*Ligules.*—Present, membranous.
*Ligule hairs.*—Absent.
*Keel.*—Absent.
*Leaf blade venation pattern.*—Parallel.
*Leaf blade color.*—Very dark green Munsell color 2.5G value of 3 chroma of 4.
*Leaf blade color* (*winter*).—Very dark green; Munsell color 2.5G value of 3 chroma of 4.
*Leaf intensity of green color after vernalization.*—Medium to Dark.
*Leaf blade hairs* (*upper side*).—Absent.
*Leaf blade hairs* (*lower side*).—Absent.
*Stem color.*—Munsell color 7.5 GY value of 7 chroma of 6.
*Ascending culm internode length.*—13.4 cm.
*Culm node pubescence.*—Absent.
*Time of flowering.*—Mar. 17, 2021 in Dallas, Tex.
*Glumes length.*—4.42 mm.
*Lemma colors.*—7.5 GY value of 6 chroma of 8.
*Palea colors.*—7.5 GY value of 6 chroma of 8.
*Ligule color.*—White/clear.

Inflorescence:
*Type.*—Panicle.
*Collar of the rachis.*—Munsell color 7.5GY value of 7 chroma of 6.
*Panicle description* (*habit; type*).—Upright; Compact.
*Panicle length.*—10.8 cm.
*Panicle diameter.*—2.4 cm.
*Color.*—7.5 GY value of 5 chroma of 4 with anthocyanin present at tips with a coloration of 5R and a value of 1 and chroma of 10.
*Stigma length.*—
*Stigma color.*—White.
*Peduncle length.*—5.8 cm.
*Pedicel length.*—5.07 mm.
*Pedicel color.*—Munsell color of 7.5GY value of 7 chroma of 5.
*Awns.*—Absent.
*Culm diameter.*—0.62 mm.
*Number of panicle bearing tillers in the culm.*—Average of 9 from 3 replications.
*Culm color.*—Munsell color 2.5G value of 5 chroma of 4.
*Culm anthocyanin coloration of the nodes and internodes.*—Anthocyanin at the nodes appears very infrequently compared to Reveille and is less intense with a shorter gradation and coloration close to 5R with a value of 4 and chroma of 2.
*Caryopsis shape.*—Sterile with no seed development.
*Florets per spike.*—3.9 on average.

Environmental resistance:
*Cold* (*injury*).—Moderately Resistant.
*Heat.*—Moderately Resistant.
*Drought.*—Moderately Resistant.
*Low fertility.*—Moderately Resistant.
*Alkalinity* (*pH*>7.5).—Highly Resistant.

Disease resistance:
*Leaf Rust* (*P. poae-nemoralis*).—Moderately Resistant.

Morphological analysis of 'DALBG 1201':

Morphological comparisons were made between 'DALBG 1201', 'Reveille', and 'Rebel Exeda' tall fescue (Table 1 and 2). A 10.2 cm plug of each cultivar was propagated into three 8-inch azalea pots filled with potting soil on Nov. 16, 2020. Pots were buried in a sandbed in a randomized complete block design on Dec. 11, 2020 to induce vernalization. Pots were removed from the sand bed on Feb. 24, 2021 and placed in a 77° F.±5° F. greenhouse. Supplemental lighting was provided with LED lights to extend daylengths to 16 hrs. The first inflorescences began emerging on March 15th (Reveille), March 17th (DALBG 1201), and March 22nd (Rebel Exeda). Four sample measurements were collected from each replicate pot for a total of 12 samples per trait. Blade leaf length (cm) and width (mm) were measured from the first fully expanded leaves before stem elongation. Plant height before stem elongation (cm) was measured from the four tallest leaves. Rhizome internode lengths (mm) were only measured on those with new shoots between the first, second, third, fourth, and fifth nodes. Rhizome diameters (mm) were measured on the fourth internode and node. The ascending culm internode length (cm) was measured between the nodes of the first and second leaves of the four tallest inflorescences. Culm diameter (mm) measured the thickness of ascending culm. Inflorescence length or plant height were measured at full maturity from the base of the plant to tip of the inflorescence. Flag leaf length (cm) and width (mm) were measured from the four tallest inflorescences in each pot. Peduncle length (cm) was measured between the flag leaf node and base of the inflorescence. Panicle diameter (cm) and length (cm) were measured from the four tallest inflorescences. Pedicel length (mm) was measured between the node of the second branching spikelet and base of the first floret. Glume length (mm) was measured between the base of a lower glume and tip of an upper glume. The number of florets per spikelet were counted randomly from one spikelet from each of four inflorescences. The number of inflorescences were counted for each pot and averaged.

Figure 2:
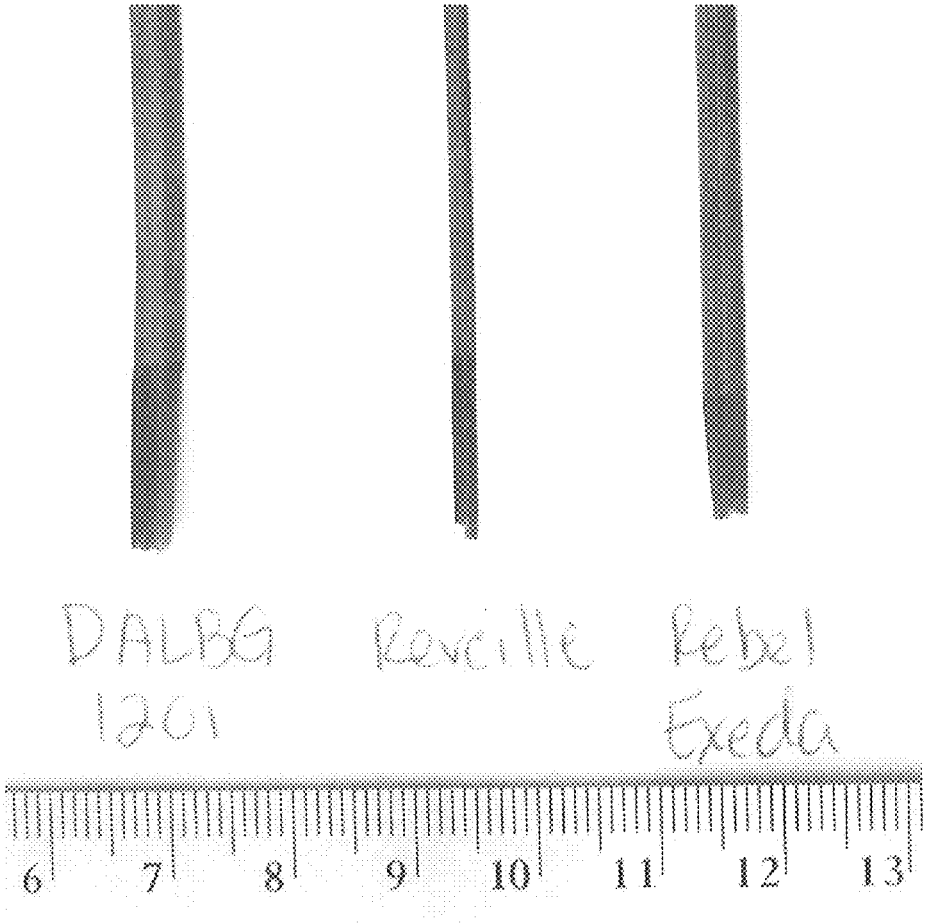
FIG. 2—Shows the leaf width differences between 'DALBG 1201', 'Reveille', and 'Rebel Exeda'.
Figure 3:
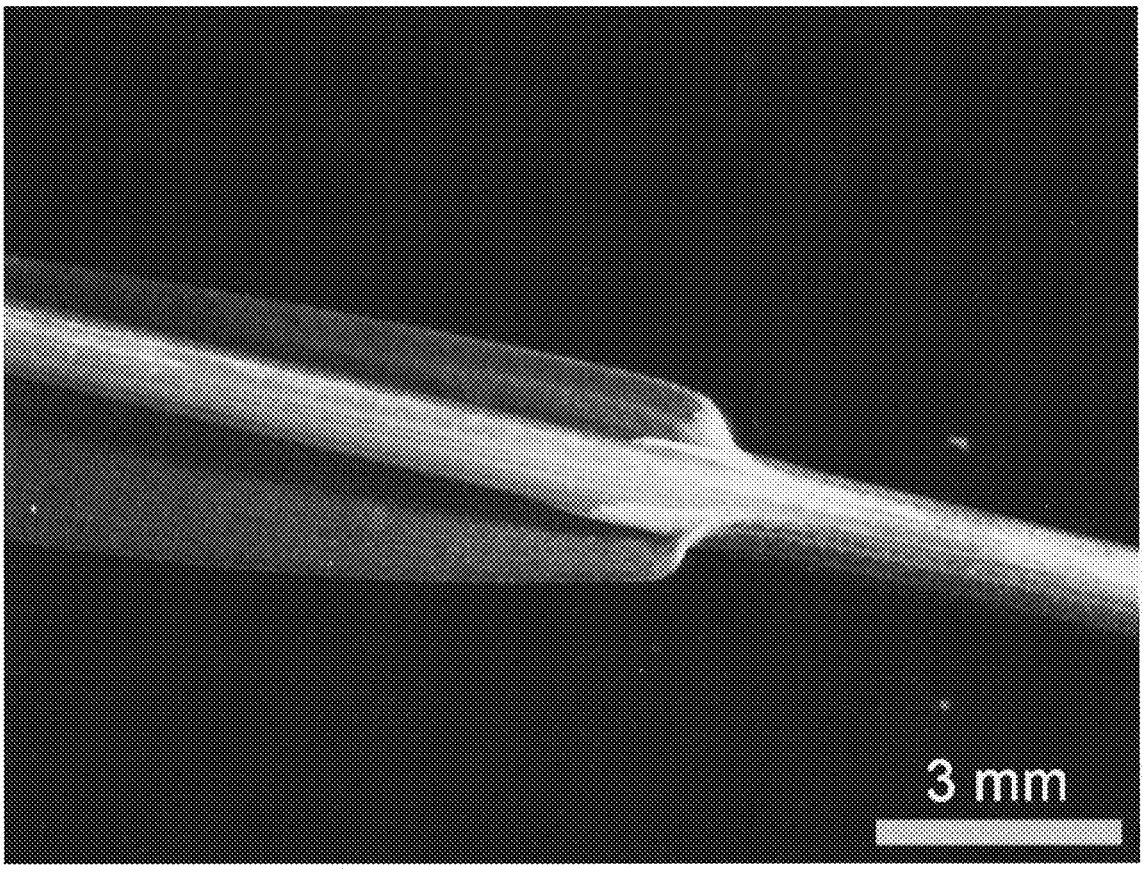
FIG. 3—Shows 'DALBG 1201's lack of auricles and shows 'DALBG 1201' has a membranous ligule at the base of each leaf FIG. 4—Shows a comparison of the inflorescence height and density between 'DALBG 1201' (left), 'Reveille' (middle), and 'Rebel Exeda' (right) photographed on Apr. 7, 2021 after 5 months of no trimming. 'DALBG 1201' exhibited fewer inflorescences on average (9) compared to 'Reveille' (26) and 'Rebel Exeda' (49)

Vegetative characteristics: 'DALBG 1201' is similar in leaf blade length to Rebel Exeda which is longer than Reveille (Table 1). The leaf blade width of 'DALBG 1201' is intermediate to 'Reveille' and 'Rebel Exeda' (Table 1 and FIG. 2). 'DALBG 1201' lacks leaf blade hairs and auricles and has a membranous ligule at the base of each leaf (FIG. 3). Natural plant height before stem elongation is similar to 'Reveille' which is taller than 'Rebel Exeda' (Table 1). Rhizome internode lengths of 'DALBG 1201' are not statistically different from 'Reveille', but the fourth internode and node diameters are larger than 'Reveille' (Table 1).

Figure 4:
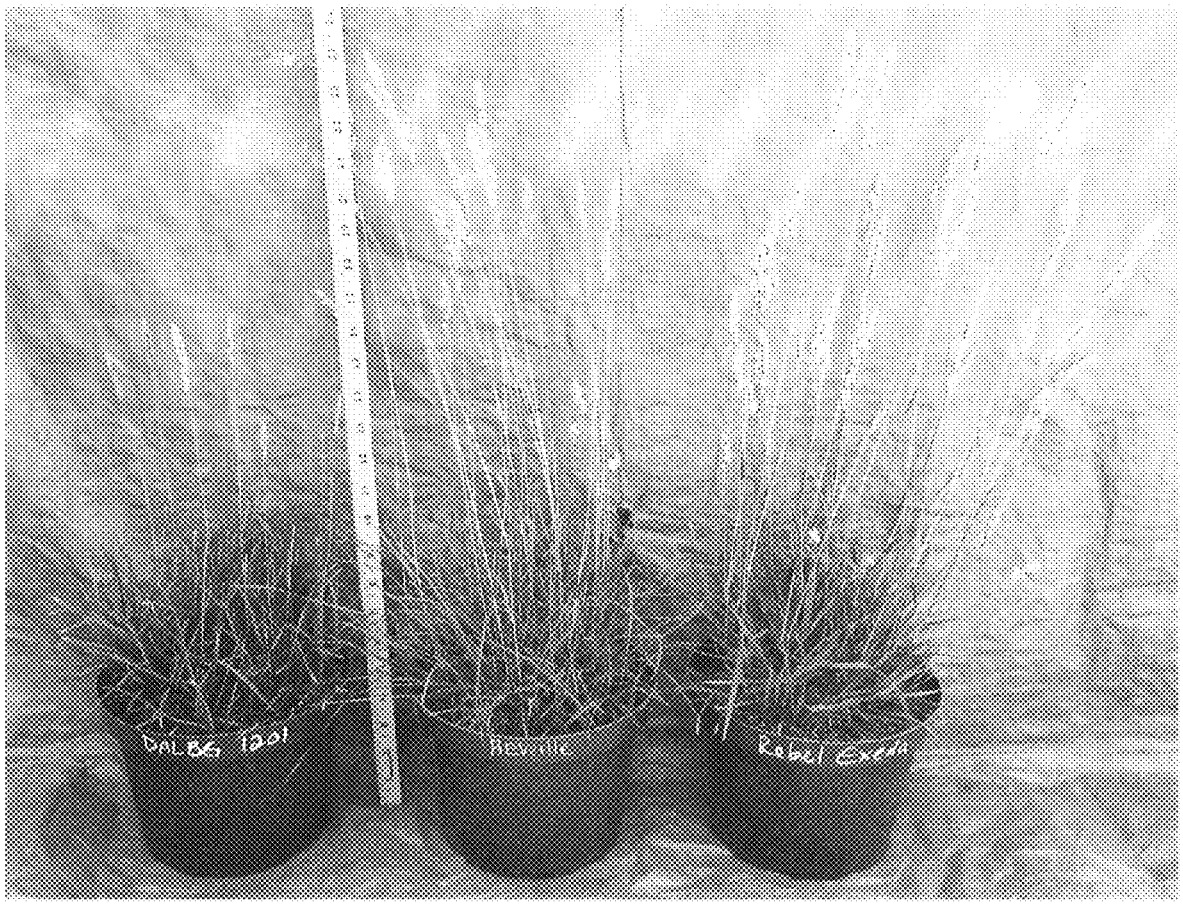
Figure 5:
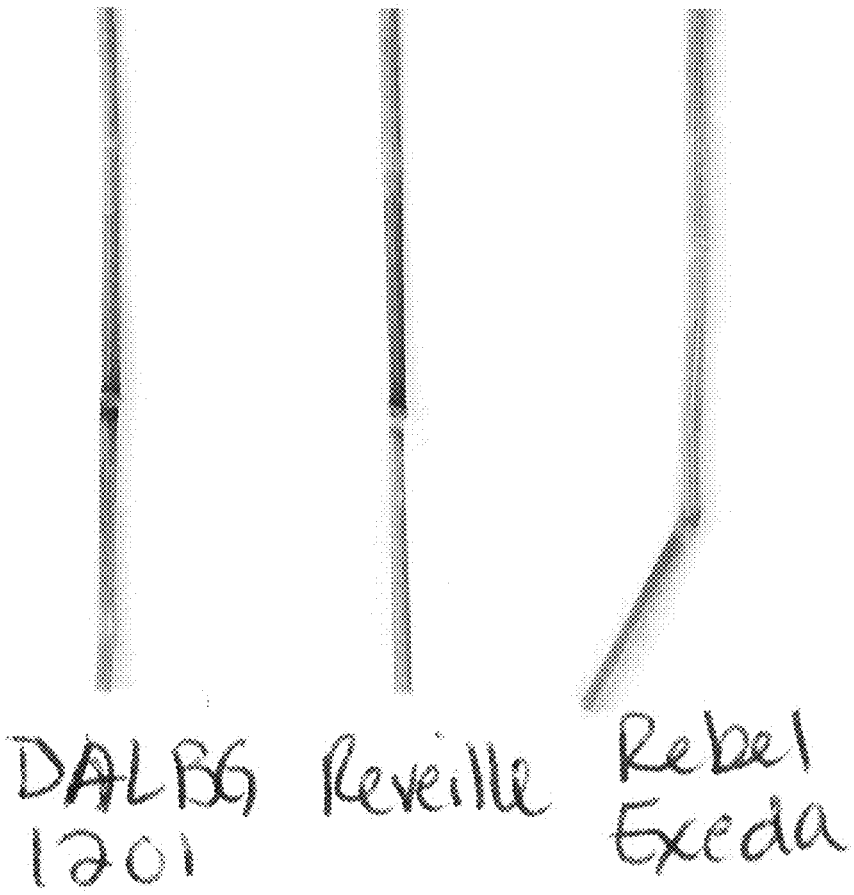
FIG. 5—Shows the ascending culm node coloration of 'DALBG 1201', 'Reveille', and 'Rebel Exeda' tall fescue.
Figure 6:
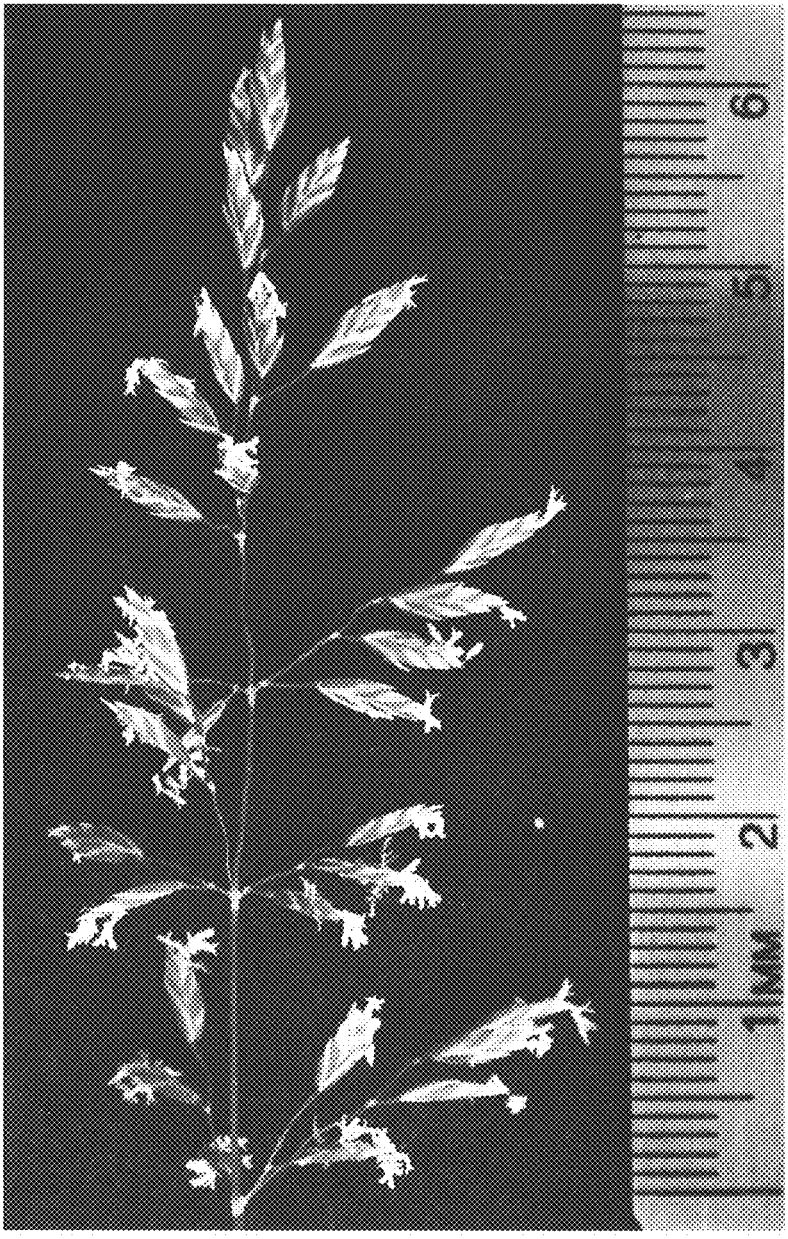
FIG. 6—Shows the immature inflorescence shape and color of 'DALBG 1201' panicle with exerted stigmas and anthers.
Figure 7:
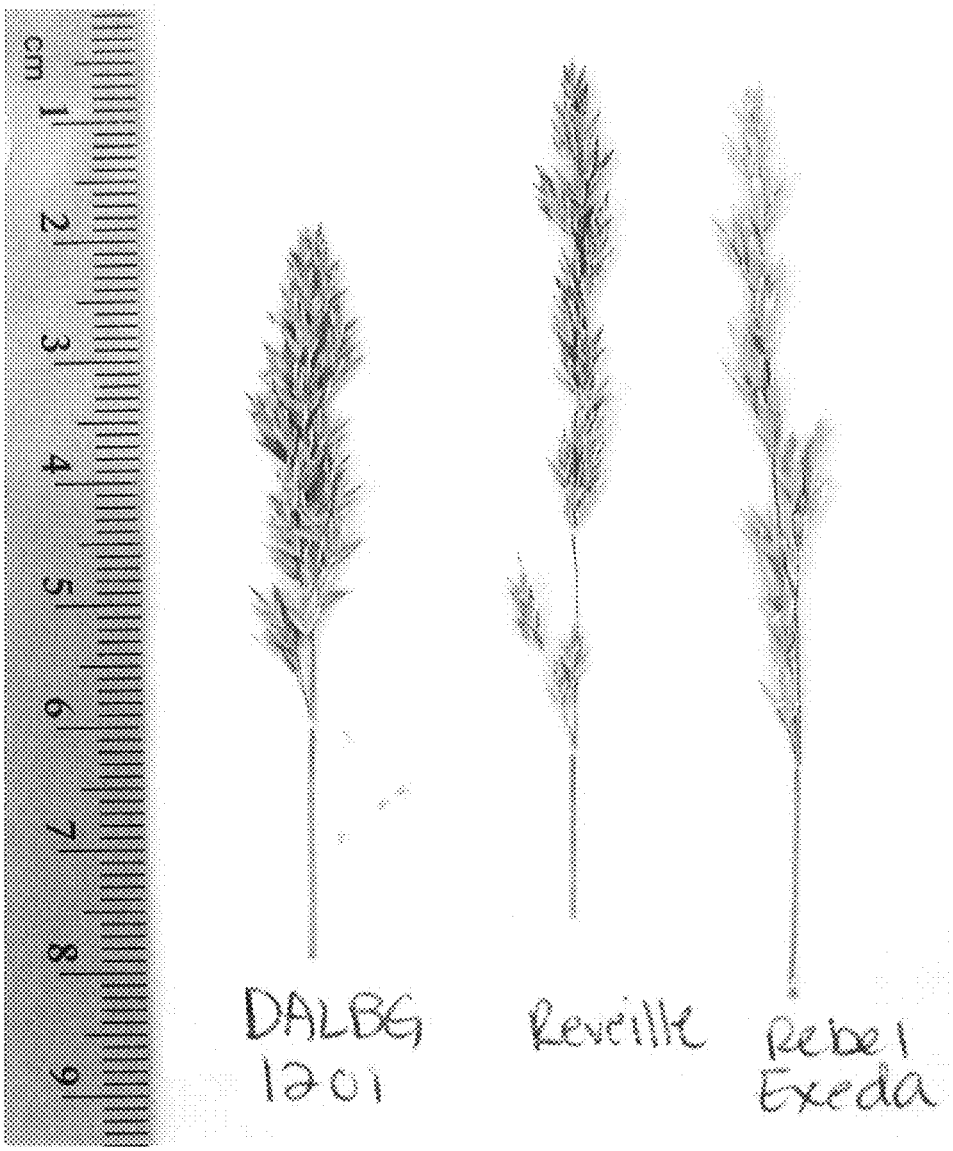
FIG. 7—Shows the mature panicle length and coloration of 'DALBG 1201', 'Reville', and 'Rebel Exeda'.
Figure 8:
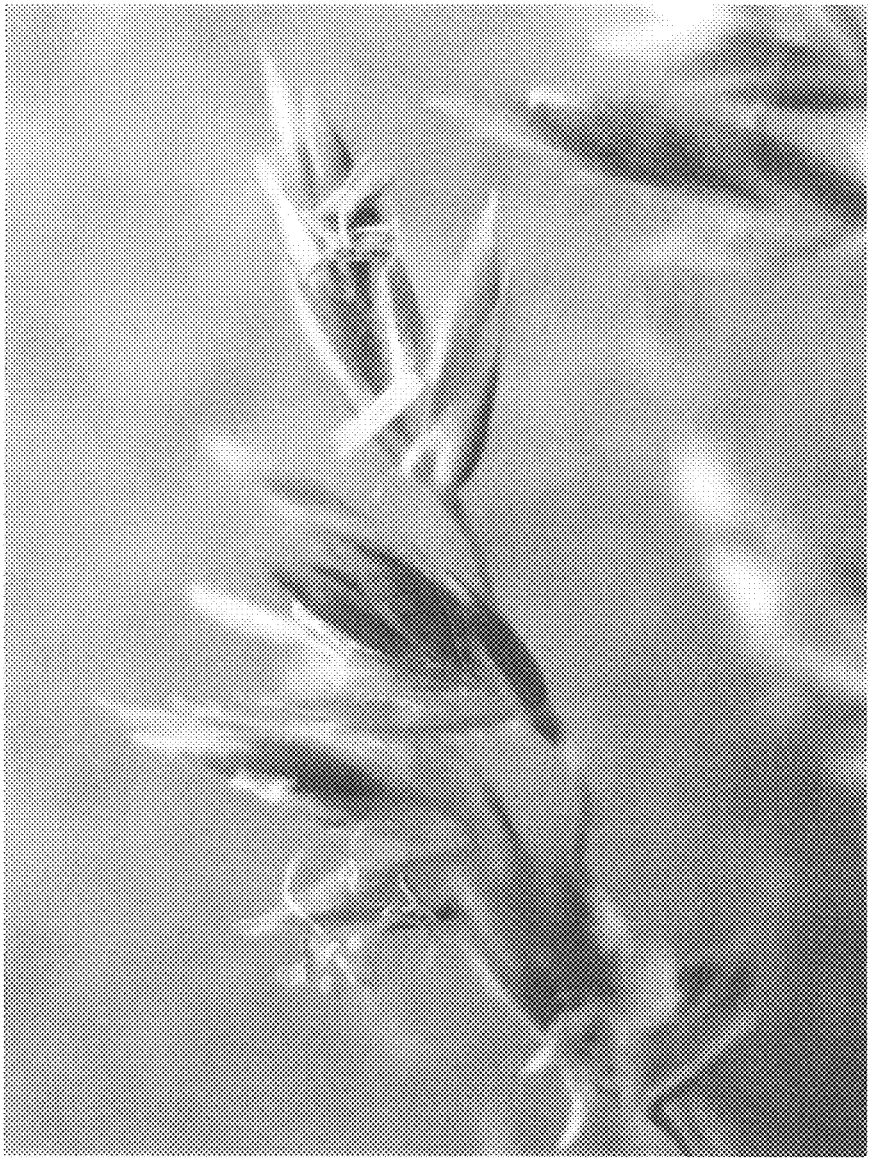
FIG. 8—Shows the anthocyanin present at the tips of maturing 'DALBG 1201' inflorescence on Mar. 26, 2020.
Figure 9:
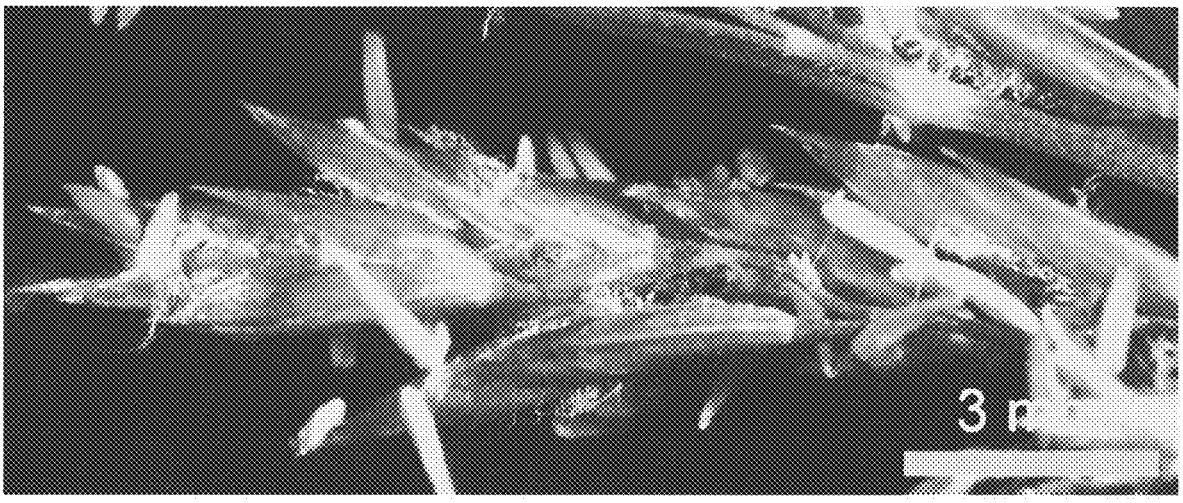
FIG. 9—Shows a microscopic image of 'DALBG 1201' spikelet florets, anthers, stigmas, and glumes.
Figure 10:
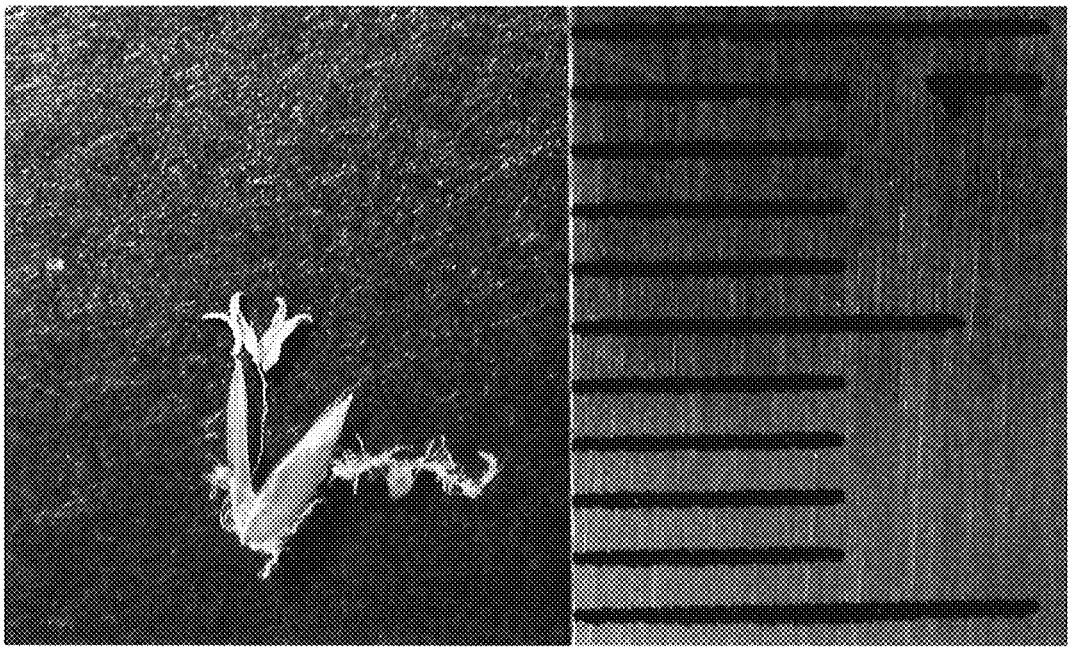
FIG. 10—Shows the immature ovary of 'DALBG 1201' and the attached stigmas and mature anthers

Floral characteristics: 'DALBG 1201' inflorescences began emerging a few days later than 'Reveille' and one week earlier than 'Rebel Exeda'. The ascending culm internode length is similar to 'Reveille' and longer than 'Rebel Exeda' (Table 2). No differences were determined for culm diameter between the three cultivars (Table 2). The mature plant height of DALBG 1201 after anthesis is more dwarf compared to 'Reveille' and 'Rebel Exeda' (Table 2 and FIG. 4) and 'DALBG 1201' exhibited fewer inflorescences on average (9) compared to 'Reveille' (26) and 'Rebel Exeda' (49). Flag leaf length and width of 'DALBG 1201' and 'Reveille' were similar and shorter and narrower than Rebel Exeda (Table 2). The peduncle length of 'DALBG 1201' is very short compared to the other two cultivars (Table 2). Compared to 'Reveille', 'DALBG 1201' has a shorter gradation of anythocyanin present at the ascending culm node and occurs infrequently compared to 'Reveille' which has a strong purple coloration on every culm (FIG. 5). Although 'DALBG 1201' has a wider panicle diameter than 'Reveille' and 'Rebel Exeda', the panicle length is statistically similar to 'Reveille' and shorter than 'Rebel Exeda' (Table 2). Although immature inflorescences of 'DALBG 1201' express no anthocyanin early after emergence (FIG. 6) it appears at the tips of florets before maturity similar to 'Reveille' (FIGS. 7 and 8). No differences in number of florets per spikelet were determined (Table 2). Glume length is statistically shorter for 'DALBG 1201' compared to 'Reveille' and 'Rebel Exeda' (Table 2 and FIGS. 9 and 10). Although anthers and stigmas are exerted in 'DALBG 1201', there is relatively little pollen which doesn't produce viable seed (sterile) (FIG. 10).

TABLE 1

Statistical analysis of vegetative traits in March 2021 between 'DALBG 1201', 'Reveille', and 'Rebel Exeda' tall fescue.

| | Leaf blade | | Plant height before stem | Rhizome internode length§ | |
|---|---|---|---|---|---|
| Cultivar | Length† cm | Width† mm | elongation‡ cm | 1st mm | 2nd mm |
| DALBG 1201 | 8.90 a | 3.28 b | 17.78 a | 11.74 | 15.76 |
| Reveille | 6.27 b | 2.10 c | 17.97 a | 12.09 | 12.39 |
| Rebel Exeda | 8.49 a | 3.71 a | 16.16 b | — | — |
| Fisher's LSD¶ | 1.50 | 0.32 | 1.37 | NS | NS |
| C.V.# | 22.80 | 12.62 | 9.52 | 20.82 | 29.38 |

| | Rhizome internode length§ | | Rhizome diameter§ | |
|---|---|---|---|---|
| Cultivar | 3rd | 4th | 4th internode mm | 4th node |
| DALBG 1201 | 13.77 | 12.11 | 0.58 a | 1.04 a |
| Reveille | 10.59 | 9.96 | 0.32 b | 0.70 b |
| Rebel Exeda | — | — | — | — |
| Fisher's LSD¶ | NS | NS | 0.10 | 0.14 |
| C.V.# | 31.97 | 43.20 | 23.78 | 18.26 |

†Blade leaf length (cm) and width (mm) were measured from the first fully expanded leaves before stem elongation.
‡Plant height before stem elongation (cm) was measured from the four tallest leaves.
§Rhizomes were not available for Rebel Exeda so DALBG 1201 was only compared to Reveille. Internode lengths and diameters were only measured from rhizomes with a new shoot.
¶Four sample measurements were collected for each replicate pot and trait for a total of 12 samples. If the ANOVA was determined to be significant at the 0.05 probability level, means were separated using Fisher's LSD.
#Coefficients of variation were calculated by dividing the root mean square error by the grand mean and multiplying by 100.

TABLE 2

Statistical analysis of floral traits in March 2021 between 'DALBG 1201', 'Reveille', and 'Rebel Exeda' tall fescue.

| Cultivar | Ascending culm internode length† cm | Culm diameter‡ mm | Inflorescence length (plant height)§ cm | Flag leaf length¶ cm | Flag leaf width¶ mm | Peduncle length# cm |
|---|---|---|---|---|---|---|
| DALBG 1201 | 13.39 a | 0.62 | 34.75 c | 2.37 b | 2.26 b | 5.75 b |
| Reveille | 11.75 ab | 0.53 | 40.64 b | 2.88 b | 2.13 b | 11.78 a |
| Rebel Exeda | 10.76b | 0.84 | 46.93 a | 4.47 a | 3.25 a | 12.85 a |
| Fisher's LSD## | 2.00 | NS | 3.94 | 0.70 | 0.38 | 1.81 |
| C.V.††† | 20.13 | 61.82 | 11.62 | 26.02 | 17.81 | 21.50 |

| Cultivar | Panicle diameter†† cm | Panicle length †† cm | Pedicel length†† mm | Florets per spike §§ no. | Glume length¶¶ mm |
|---|---|---|---|---|---|
| DALBG 1201 | 2.40 a | 5.18 b | 5.07 a | 3.92 | 4.42 b |
| Reveille | 1.83 b | 5.33 b | 4.08 b | 4.75 | 3.32 c |
| Rebel Exeda | 1.70 b | 7.37 a | 5.22 a | 4.17 | 5.81 a |
| Fisher's LSD## | 0.31 | 1.22 | 0.81 | NS | 0.59 |
| C.V.††† | 18.92 | 24.53 | 20.33 | 28.57 | 15.70 |

†The ascending culm internode length (cm) was measured between the nodes of the first and second leaves of the four tallest inflorescences.
‡Culm diameter (mm) measured the thickness of ascending culm.
§Inflorescence length or plant height were measured at full maturity from the base of the plant to tip of the inflorescence.
¶Flag leaf length (cm) and width (mm) were measured from the four tallest inflorescences in each pot.
#Peduncle length (cm) was measured between the flag leaf node and base of the inflorescence.
††Panicle diameter (cm) and length (cm) were measured from the four tallest inflorescences.
‡‡Pedicel length (mm) was measured between the node of the second branching spikelet and base of the first floret.
§§The number of florets per spikelet were counted randomly from one spikelet from each of four inflorescences.
¶¶Glume length (mm) was measured between the base of a lower glume and tip of an upper glume.
Four sample measurements were collected for each replicate pot and trait for a total of 12 samples. If the ANOVA was determined to be significant at the 0.05 probability level, means were separated using Fisher's LSD.
†††Coefficients of variation were calculated by dividing the root mean square error by the grand mean and multiplying by 100.

Establishment and turfgrass performance evaluation:

47 experimental hybrids including 'DALBG 1201', along with five Texas bluegrass ecotypes ('TAES 5679', 5681-5684), six Kentucky bluegrass genotypes ('H8G-J86', 'PTDF-22-B-2', 'H86-712', 'TAES 5701', 'TAES 5706', and 'TAES 5709'), two commercial hybrid bluegrass checks ('Reveille', 'Thermal Blue Blaze'), and 'Rebel Exeda' tall fescue were assembled for a multi-location test. Entries were planted under full sunlight in a randomized complete block experimental design with three replications in each of five test locations and were evaluated over a period of 3 year from 2010 to 2012. Test sites were located in Auburn, Ala., Dallas, Tex., Starkville, Miss., Raleigh, N.C., and Knoxville, Tenn.

For experimental hybrids, a 7.62-cm by 7.62-cm plug was planted in a 0.61-m by 0.61-m plot during September to October 2009. Commercial hybrid bluegrass cultivars were established by seed, planted at a rate of 14.65 g m-2, and 'Rebel Exeda' was seeded at 29.29 g m-2. Plots were irrigated to promote establishment in Year 1 of the trial, with at least 2.54 cm of irrigation applied weekly to supplement rainfall. Thereafter, irrigation was provided to prevent dormancy or stress. After initial establishment, plots were mowed at a 5.08 cm to 6.35 cm height. Nitrogen (N) was applied at rate of 19.53 to 29.29 g m-2 each year in split doses once in each fall, winter, and spring growing seasons. A weed management protocol was implemented according to local weed pressure at each test location. No preventative or curative pesticides were used during the course of the study to control insect or disease problems. Data for average monthly air temperature and precipitation from 2010 to 2012 were collected from a local weather station at each test location.

Turfgrass performance data were collected on a monthly basis from 2010 to 2012, but the frequency of data collection varied by location. Traits included overall turfgrass quality (1=poor; 9=ideal), seasonal color (1=straw brown; 9=dark green), shoot density (1=poor; 9=maximum density), and leaf texture (1=coarse; 9=fine). Summer turfgrass quality data were derived from the turfgrass quality ratings for the months of June to September (2010-2012) for each test location. Data for 'DALBG 1201' and the three commercial checks are presented in Tables 3-7. All of the datasets were analyzed using SAS 9.3 (SAS Institute, 2009). Means were compared using Fisher's LSD at the a=0.05 probability level. For each trait×location analysis, entries with means in the top statistical group were followed by the letter a.

Based on the average air temperature and precipitation data for the months of June through September each year (2010 to 2012), Dallas had the warmest average temperature, followed by Starkville, Auburn, Raleigh, and Knoxville. The Dallas location also had the least amount of precipitation over the 3 year, followed by Auburn, Raleigh, Knoxville, and Starkville.

Traits and characteristics of 'DALBG 1201':

*Turf quality.—*

The turfgrass quality for 'DALBG 1201' was statistically superior to 'Reveille' and 'Thermal Blue Blaze' in four test locations (Auburn, Ala., Starkville, Miss., Raleigh, N.C., Dallas, Tex.), and was in the same statistical group in Knoxville, Tenn. (Table 3). The turfgrass quality of 'DALBG 1201' was statistically similar to 'Rebel Exeda' at Auburn, Starkville, and Knoxville and was superior in Dallas. When averaged across all locations, the turfgrass quality of 'DALBG 1201' was statistically superior than the commercial checks 'Thermal Blue Blaze', 'Reveille', and 'Rebel Exeda'.

Summer turfgrass quality for 'DALBG 1201' was superior to 'Reveille' in Auburn, Raleigh, and Knoxville and was statistically similar in Starkville and Dallas (Table 4). 'DALBG 1201' outperformed 'Thermal Blue Blaze' in Raleigh, Knoxville, and Dallas and was statistically similar in Auburn and Starkville. 'DALBG 1201' outperformed 'Rebel Exeda' in Knoxville and Dallas and exhibited statistically similar summer turfgrass quality in Auburn, Starkville, and Raleigh. The 3-yr average across all locations showed that 'DALBG 1201' performed significantly better than the commercial checks. The significantly superior performance of 'DALBG 1201' in Auburn and Dallas, two of the warmest and driest locations, suggests that 'DALBG 1201' has improved summer stress tolerance. Improved summer performance of 'DALBG 1201' likely results from it being an $F_1$ hybrid from a cross between locally adapted ecotypes of Texas bluegrass and Kentucky bluegrass collected from Texas.

*Seasonal color.—*

'DALBG 1201' was in the top statistical group across all five test locations seasonal color (Table 5). With an average color rating of 7.3, 'DALBG 1201' was statistically darker green than 'Reveille' (average rating of 6.2) and 'Thermal Blue Blaze' (average rating of 6.1) across all five test locations. Compared with 'Rebel Exeda', the color rating of 'DALBG 1201' was in the same statistical group at four out of five test locations except at Auburn, where 'DALBG 1201' was statistically darker green.

*Shoot density.—*

Shoot density data were collected at four locations (Table 6). Mean shoot density of 'DALBG 1201' was significantly higher than 'Reveille' and 'Thermal Blue Blaze' in Raleigh and Dallas. 'DALBG 1201' was statistically similar to 'Rebel Exeda' in all locations. On average, the shoot density rating of 'DALBG 1201' (7.1) was significantly higher than that of 'Reveille' (6.1) and 'Thermal Blue Blaze' (5.6) and was comparable to 'Rebel Exeda' (6.8).

*Leaf texture.—*

With an average leaf texture rating of 6,5, 'DALBG 1201' had a significantly finer leaf texture than 'Rebel Exeda' (4.0) across all test locations (Table 7). The leaf texture rating for 'DALBG 1201' was in the same statistical group as 'Reveille' at all five test locations. Compared with 'Thermal Blue Blaze', the leaf texture rating for 'DALBG 1201' was in the same statistical group at four locations except Dallas, where 'DALBG 1201' had a significantly finer leaf texture (5.7). The leaf texture of 'DALBG 1201', then, is comparable to the commercially available hybrid bluegrass varieties included in the study but significantly finer than the tall fescue check.

*Disease susceptibility.—*

Rust (*Puccinia* spp.) was only observed in Auburn, during the months of May (2010) and April (2011), and Raleigh, during the months of April and June (2012). 'DALBG 1201' and the commercial checks exhibited no disease damage in 2010 and 2011 in Auburn. In Raleigh, no rust was observed on 'Rebel Exeda'. 'DALBG 1201' (7%), 'Thermal Blue Blaze' (7%), and 'Reveille' (5%) showed minimal rust damage in Raleigh, N.C. (data not shown).

*Genotype×Environment Stability Analysis.—*

Stability was defined as consistently superior performance of a genotype across varying environments (poorest to best) based on the performance of traits under consideration. Superior performance in the poorest environments and higher levels of stability (lower slope coefficient) indicates high stress tolerance and wide adaption of a genotype across environments, traits that are highly desirable when breeding improved stress tolerant cultivars.

Stability analysis of turfgrass quality indicated that Dallas represented the poorest environment and that. Knoxville was the best. Turfgrass quality ratings for 'DALBG 1201' were not only higher in Dallas relative to all three commercial checks (FIG. 1*a*), but 'DALBG 1201' also had the lowest slope coefficient of 0.698, indicating the highest stability across locations.

For shoot density, 'DALBG 1201' outperformed all three commercial checks under poorest environments (Auburn), indicating its potential for stress tolerance, and had the second highest stability across locations next to 'Rebel Exeda' as indicated by the slope coefficient of 1.064 (FIG. 1*b*). For seasonal color, although 'DALBG 1201' had highest cultivar mean across all five locations and its slope indicated reasonable stability (FIG. 1*c*), its coefficient of determination (r2) was low, suggesting that the linear regression model did not fit the data. Nonlinearity has been shown to be an important tool in analyzing genotype×environment interactions in other crops and systems (Yang, 2014), and it appears that 'DALBG 1201' is following a nonlinear regression for the color response. For leaf texture, all three hybrid bluegrasses ('DALBG 1201', 'Reveille', and 'Thermal Blue Blaze') outperformed 'Rebel Exeda' when evaluated at the location with the poorest environmental conditions (Dallas). 'DALBG 1201' had the second-lowest slope coefficient of 0.967 next to 'Reveille' (b=0.957) and was more stable across locations relative to 'Thermal Blue Blaze' and 'Rebel Exeda' (FIG. 1*d*).

TABLE 3

Mean turfgrass quality for 'DALBG 1201' and three commercial checks for five test locations.

| | I-9 | | | | | |
|---|---|---|---|---|---|---|
| Entry | Auburn, AL | Starkville, MS | Raleigh, NC | Knoxville, TN | Dallas, TX | Avg.‡ |
| DALBG 1201 | 6.8a* | 5.6a | 6.3b | 8.0a | 5.6a | 6.5a |
| Rebel Exeda§ | 6.7a | 5.4ab | 6.8a | 8.0a | 4.2b | 6.2b |
| Reveille§ | 5.7b | 5.0bc | 5.2c | 7.9a | 4.5b | 5.7c |
| Thermal Blue Blaze§ | 6.0b | 4.6c | 4.9c | 8.1a | 3.4c | 5.4d |
| LSD (0.05) | 0.6 | 0.5 | 0.5 | 0.3 | 0.7 | 0.2 |
| CV, %¶ | 9.6 | 9.9 | 8.1 | 3.8 | 16.4 | 9.0 |

*Significant at the 0.05 probability level.

†Scale of 1-9, where 1 = poor, 9 = ideal, and 5 was the minimum acceptable. Mean represents turfgrass quality data for years 2010, 2011, and 2012 at each location.

‡Average turfgrass quality of each entry across all locations from 2010 to 2012.

§Commercial checks included are 'Rebel Exeda' tall fescue and 'Reveille' and 'Thermal Blue Blaze' hybrid bluegrasses.

¶CV (coefficient of variation) indicates the percentage variation of the mean in each column.

TABLE 4

Mean summer turfgrass quality ratings for 'DALBG 1201' and three commercial checks for five test locations

| | 1-9 | | | | | |
|---|---|---|---|---|---|---|
| Entry | Auburn, AL | Starkville, MS | Raleigh, NC | Knoxville, TN | Dallas, TX | Avg.‡ |
| DALBG 1201 | 6.7a* | 5.0a | 6.5a | 8.6a | 5.1a | 6.1a |
| Rebel Exeda§ | 6.4a | 5.0a | 7.1a | 8.0b | 4.0b | 5.9a |
| Reveille§ | 5.7b | 4.7a | 5.1b | 8.2b | 4.5ab | 5.3b |
| Thermal Blue Blaze§ | 6.1a | 4.3a | 5.1b | 8.1b | 3.1c | 5.0b |

TABLE 4-continued

Mean summer turfgrass quality ratings for 'DALBG 1201' and three commercial checks for five test locations

| | 1-9 | | | | | |
|---|---|---|---|---|---|---|
| Entry | Auburn, AL | Starkville, MS | Raleigh, NC | Knoxville, TN | Dallas, TX | Avg.‡ |
| LSD (0.05) | 0.6 | 0.7 | 0.7 | 0.3 | 0.8 | 0.3 |
| CV, %¶ | 10.1 | 12.4 | 11.8 | 2.1 | 19.4 | 10.8 |

*Significant at the 0.05 probability level.

†Scale of 1-9, where 1 = poor, 9 = ideal, and 5 was the minimum acceptable. Mean represented turfgrass quality data for Auburn, AL (2010, 2011, 2012), Dallas, TX (2010. 2011, 2012), Starkville, MS (2010, 2011), Raleigh, NC (2010, 2011, 2012), and Knoxville, TN (2010, 2011), from the months June through September. Auburn data from 2010 and 2012 only included the months of June through August. Dallas data from 2010 only included the months of August and September.

‡Average turfgrass quality of 'DALBG 1201' and three commercial checks across all locations from 2010 to 2012.

§Commercial checks included are 'Rebel Exeda' tall fescue and 'Reveille' and 'Thermal Blue Blaze' hybrid bluegrasses.

CV (coefficient of variation) indicates the percentage variation of the mean in each column.

TABLE 5

Mean seasonal color for 'DALBG 1201' and three commercial checks for five test locations.

| | 1-9 | | | | | |
|---|---|---|---|---|---|---|
| Entry | Auburn, AL | Starkville, MS | Raleigh, NC | Knoxville, TN | Dallas, TX | Avg.‡ |
| DALBG 1201 | 8.1a* | 6.5a | 7.2a | 7.5a | 7.0a | 7.3a |
| Rebel Exeda¶ | 7.2b | 6.8a | 7.3a | 7.3ab | 7.0a | 7. 1a |
| Reveille¶ | 6.4c | 6.0b | 6.1b | 6.5c | 6.1b | 6.2b |
| Thermal Blue Blaze¶ | 6.2c | 5.9b | 6.0b | 6.8bc | 5.7b | 6.1b |
| LSD (0.05) | 0.6 | 0.4 | 0.5 | 0.5 | 0.5 | 0.3 |
| CV, %# | 11.3 | 6.6 | 9.2 | 7.5 | 10.5 | 9.3 |

*Significant at the 0.05 probability level.

†Scale of 1-9, where 1 = straw brown, 9 = dark green. Mean represented color data from 2010 to 2012 at each location, Starkville, MS data was presented for 2010 and 2011.

§Average seasonal color a.cross all locations from 2010 to 2012.

¶Commercial checks included are 'Rebell Exeda' tall fescue, and 'Reveille' and 'Thermal Blue Blaze' hybrid bluegrasses. # CV (coefficient of variation) indicates the percentage variation of the mean in each column.

TABLE 6

Mean shoot density for 'DALBG 1201' and three commercial checks for four test locations.

| | 1-9 | | | | |
|---|---|---|---|---|---|
| Entry | Auburn, AL | Starkville, MS | Raleigh, NC | Dallas, TX | Avg.‡ |
| DALBG 1201 | 3.7a | 8.5a | 8.2a | 6.7a | 7.1.a |
| Rebel Exeda¶ | 3.0a | 8.5a | 8.2a | 5.9ab | 6.8a |
| Reveille¶ | 2.7a | 8.3a | 6.2b | 5.7b | 6.1b |
| Thermal Blue Blaze¶ | 2.3a | 8.5a | 5.8b | 4.6c | 5.6c |
| LSD (0.05) | 1.3 | 0.9 | 1.1 | 0.8 | 0.5 |
| CV, %# | 25.0 | 9.6 | 13.9 | 13.9 | 13.5 |

*Significant at the 0.05 probability level.

‡Scale of 1-9, where 9 = maximum density. Mean represented density data from Auburn, AL (2010), Dallas, TX (2010, 2011, 2012), Starkville, MS (2010, 2011), and Raleigh, NC (2011, 2012).

§Average seasonal color and shoot density across all locations from 2010 to 2012.

¶Commercial cheeks included are 'Rebel Exeda' tall fescue, and 'Reveille' and 'Thermal Blue Blaze' hybrid bluegrasses.

#CV (coefficient of variation) indicates the percentage variation of the mean in each column.

TABLE 7

Mean leaf texture for 'DALBG 1201' and three commercial checks at five test locations.

| Entry | 1-9 | | | | | |
|---|---|---|---|---|---|---|
| | Auburn, AL | Starkville, MS | Raleigh, NC | Knoxville, TN | Dallas, TX | Avg.‡ |
| DALBG 1201 | 6.2a* | 5.8a | 7.0a | 8.7a | 5.7a | 6.5a |
| Rebel Exeda¶ | 3.0b | 4.3b | 5.0b | 7.0b | 2.3c | 4.0b |
| Reveille¶ | 6.0a | 5.5a | 7.0a | 8.3a | 5.7a | 6.3a |
| Thermal Blue Blaze¶ | 6.6a | 5.8a | 7.0a | 8.3a | 4.0b | 6.3a |

TABLE 7-continued

Mean leaf texture for 'DALBG 1201' and three commercial checks at five test locations.

| Entry | 1-9 | | | | | |
|---|---|---|---|---|---|---|
| | Auburn, AL | Starkville, MS | Raleigh, NC | Knoxville, TN | Dallas, TX | Avg.‡ |
| LSD (0,05) | 0.9 | 0.6 | 0.3 | 1.3 | 0.9 | 0.4 |
| CV, %# | 16.2 | 9.3 | 13.0 | 8.8 | 11.3 | 11.6 |

*Significant at the 0.05 probability level.

†Scale of 1-9, where 1 = coarse, 9 = fine. Means represented data from Auburn, AL (2010, 2011, 2012), Dallas, TX (2012), Starkville, MS (2010, 2011), Raleigh, NC (2012), and Knoxville, TN (2011).

‡Average leaf texture across all locations from 2010 to 2012.

§Commercial checks included are 'Rebel Exeda' tall fescue, and 'Reveille' and 'Thermal Blue Blaze' hybrid bluegrasses.

¶CV (coefficient of variation) indicates the percentage variation of the mean in each column.

What is claimed is:

1. A new and distinct interspecific hybrid variety of bluegrass named 'DALBG 1201' as shown and described herein.

* * * * *